(12) United States Patent
Melsheimer

(10) Patent No.: US 8,075,497 B2
(45) Date of Patent: Dec. 13, 2011

(54) WIRE GUIDE HAVING DISTAL COUPLING TIP

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 197 days.

(21) Appl. No.: 11/507,805

(22) Filed: Aug. 22, 2006

(65) Prior Publication Data

US 2007/0088328 A1   Apr. 19, 2007

Related U.S. Application Data

(60) Provisional application No. 60/833,144, filed on Jul. 25, 2006, provisional application No. 60/711,261, filed on Aug. 25, 2005.

(51) Int. Cl.
| A61M 25/00 | (2006.01) |
| A61M 25/16 | (2006.01) |
| A61M 25/18 | (2006.01) |
| A61M 39/00 | (2006.01) |
| A61M 39/10 | (2006.01) |

(52) U.S. Cl. .................. 600/585; 604/533; 604/534
(58) Field of Classification Search .......... 600/585; 604/533–539
See application file for complete search history.

(56) References Cited

U.S. PATENT DOCUMENTS

| 2,657,691 | A | * | 11/1953 | Nordstrom, Jr. ............ 606/108 |
| 3,521,620 | A | | 7/1970 | Cook |
| 3,547,103 | A | | 12/1970 | Cook |
| 3,656,680 | A | | 4/1972 | Nomura |
| 3,739,784 | A | | 6/1973 | Itoh |
| 3,890,977 | A | | 6/1975 | Wilson |
| 4,548,206 | A | | 10/1985 | Osborne |
| 4,569,347 | A | * | 2/1986 | Frisbie ........................ 606/108 |
| 4,601,713 | A | | 7/1986 | Fuqua |
| 4,650,472 | A | | 3/1987 | Bates |
| 4,665,906 | A | | 5/1987 | Jervis |
| 4,824,435 | A | * | 4/1989 | Giesy et al. .................. 604/500 |
| 4,921,483 | A | | 5/1990 | Wijay et al. |
| 4,925,445 | A | | 5/1990 | Sakamoto et al. |
| 4,934,380 | A | | 6/1990 | De Toledo |

(Continued)

FOREIGN PATENT DOCUMENTS

EP   0 436 303 A1   11/1990

(Continued)

OTHER PUBLICATIONS

International Search Report—PCT/US2006/040843 (Jan. 31, 2007).

(Continued)

*Primary Examiner* — Max Hindenburg
*Assistant Examiner* — Adam Eiseman
(74) *Attorney, Agent, or Firm* — Brinks Hofer Gilson & Lione

(57) ABSTRACT

A coupling wire guide structured to be slidably coupled to a previously introduced wire guide during intracorporeal procedures. The coupling wire guide includes a main body and a tip portion, the tip portion having first, second and third sections. The first section is connected to the main body, while the second section interconnects the first and third sections. The third section defines an axial passageway having a distal opening and a proximal opening. The axial passageway is sized to receive the previously introduced wire guide therein. The second section includes a strip sized to leave an open area in communication with the proximal opening.

30 Claims, 5 Drawing Sheets

U.S. PATENT DOCUMENTS

| | | | |
|---|---|---|---|
| 4,984,581 A | 1/1991 | Stice | |
| 5,003,990 A * | 4/1991 | Osypka | 600/585 |
| 5,069,226 A | 12/1991 | Yamauchi et al. | |
| 5,105,818 A | 4/1992 | Christian et al. | |
| 5,129,890 A | 7/1992 | Bates et al. | |
| 5,131,407 A | 7/1992 | Ischinger et al. | |
| 5,159,861 A | 11/1992 | Anderson | |
| 5,213,111 A | 5/1993 | Cook et al. | |
| 5,234,003 A | 8/1993 | Hall | |
| 5,242,759 A | 9/1993 | Hall | |
| 5,243,996 A | 9/1993 | Hall | |
| 5,251,640 A | 10/1993 | Osborne | |
| 5,267,958 A | 12/1993 | Buchbinder et al. | |
| 5,306,261 A | 4/1994 | Alliger et al. | |
| 5,318,527 A | 6/1994 | Hyde et al. | |
| 5,325,746 A | 7/1994 | Anderson | |
| 5,328,472 A | 7/1994 | Steinke et al. | |
| 5,328,480 A | 7/1994 | Milker et al. | |
| 5,344,413 A * | 9/1994 | Allman et al. | 604/523 |
| 5,354,257 A | 10/1994 | Roubin et al. | |
| 5,383,853 A * | 1/1995 | Jung et al. | 604/103.04 |
| 5,402,799 A | 4/1995 | Colon et al. | |
| 5,449,362 A * | 9/1995 | Chaisson et al. | 606/108 |
| 5,456,680 A | 10/1995 | Taylor et al. | |
| 5,488,959 A | 2/1996 | Ales | |
| 5,597,378 A | 1/1997 | Jervis | |
| 5,667,521 A * | 9/1997 | Keown | 606/194 |
| 5,738,667 A | 4/1998 | Solar | |
| 5,762,070 A | 6/1998 | Nagamatsu | |
| 5,776,079 A | 7/1998 | Cope et al. | |
| 5,776,100 A | 7/1998 | Forman | |
| 5,797,857 A | 8/1998 | Obitsu | |
| 5,810,876 A | 9/1998 | Kelleher | |
| 5,827,225 A | 10/1998 | Ma Schwab | |
| 5,873,842 A | 2/1999 | Brennen et al. | |
| 5,882,333 A | 3/1999 | Schaer et al. | |
| 5,891,056 A * | 4/1999 | Ramzipoor | 600/585 |
| 5,893,868 A * | 4/1999 | Hanson et al. | 623/1.11 |
| 5,993,424 A | 11/1999 | Lorenzo et al. | |
| 5,997,526 A | 12/1999 | Giba et al. | |
| 6,007,517 A | 12/1999 | Anderson | |
| 6,010,464 A * | 1/2000 | Galdonik et al. | 600/585 |
| 6,139,510 A | 10/2000 | Palermo | |
| 6,217,567 B1 | 4/2001 | Zadno-Azizi et al. | |
| 6,221,066 B1 * | 4/2001 | Ferrera et al. | 606/1 |
| 6,248,092 B1 | 6/2001 | Miraki et al. | |
| 6,254,549 B1 * | 7/2001 | Ramzipoor | 600/585 |
| 6,254,550 B1 | 7/2001 | McNamara et al. | |
| 6,290,693 B1 | 9/2001 | Jung, Jr. et al. | |
| 6,306,141 B1 | 10/2001 | Jervis | |
| 6,309,404 B1 | 10/2001 | Krzyzanowski | |
| 6,348,041 B1 | 2/2002 | Klint | |
| 6,348,045 B1 | 2/2002 | Malonek et al. | |
| 6,383,146 B1 | 5/2002 | Klint | |
| 6,471,697 B1 | 10/2002 | Lesh | |
| 6,475,167 B1 | 11/2002 | Fleming et al. | |
| 6,500,130 B2 | 12/2002 | Kinsella et al. | |
| 6,502,606 B2 | 1/2003 | Klint | |
| 6,517,518 B2 | 2/2003 | Nash et al. | |
| 6,530,899 B1 | 3/2003 | Savage | |
| 6,569,151 B1 * | 5/2003 | Nash et al. | 604/533 |
| 6,596,963 B2 | 7/2003 | Kelly | |
| 6,605,049 B1 | 8/2003 | Wagner et al. | |
| 6,613,002 B1 | 9/2003 | Clark et al. | |
| 6,638,372 B1 | 10/2003 | Abrams et al. | |
| 6,682,608 B2 | 1/2004 | Abrams et al. | |
| 6,805,676 B2 | 10/2004 | Klint | |
| 6,872,192 B2 | 3/2005 | Nash et al. | |
| 7,074,197 B2 | 7/2006 | Reynolds et al. | |
| 7,076,285 B2 | 7/2006 | Windheuser et al. | |
| 7,229,431 B2 | 6/2007 | Houser et al. | |
| 2002/0058888 A1 | 5/2002 | Biagtan et al. | |
| 2002/0169457 A1 | 11/2002 | Quinn | |
| 2003/0028127 A1 | 2/2003 | Balzum et al. | |
| 2003/0120208 A1 | 6/2003 | Houser et al. | |
| 2004/0073108 A1 | 4/2004 | Saeed et al. | |
| 2004/0116957 A1 | 6/2004 | Nishide | |
| 2004/0199087 A1 | 10/2004 | Swain et al. | |
| 2004/0215208 A1 | 10/2004 | Foushee et al. | |
| 2005/0027212 A1 | 2/2005 | Segner et al. | |
| 2005/0075647 A1 | 4/2005 | Walters et al. | |
| 2005/0143770 A1 | 6/2005 | Carter et al. | |
| 2005/0148902 A1 | 7/2005 | Minar et al. | |
| 2005/0197663 A1 | 9/2005 | Soma et al. | |
| 2005/0209533 A1 * | 9/2005 | Lorenz | 600/585 |
| 2005/0267442 A1 * | 12/2005 | Von Oepen | 604/509 |
| 2006/0100544 A1 | 5/2006 | Ayala et al. | |
| 2006/0100545 A1 | 5/2006 | Ayala et al. | |
| 2007/0060908 A1 | 3/2007 | Webster et al. | |
| 2007/0167065 A1 | 7/2007 | Melsheimer et al. | |
| 2007/0185414 A1 | 8/2007 | Urbanski et al. | |
| 2007/0191790 A1 | 8/2007 | Eells et al. | |

FOREIGN PATENT DOCUMENTS

| | | |
|---|---|---|
| EP | 0 829 269 A1 | 3/1998 |
| EP | 1 057 500 A1 | 12/2000 |
| EP | 1 428 546 A2 | 6/2004 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 01/03764 A1 | 1/2001 |
| WO | WO 02 094364 A2 | 11/2002 |
| WO | WO2004/033016 | 4/2004 |
| WO | WO 2004/049970 A2 | 6/2004 |
| WO | WO 2005/011530 A1 | 2/2005 |
| WO | WO 2005/011788 A1 | 2/2005 |
| WO | WO 2005/025660 A1 | 3/2005 |
| WO | WO 2005/089852 A1 | 9/2005 |
| WO | WO 2007/084474 A1 | 7/2007 |
| WO | WO 2007/089891 A3 | 8/2007 |
| WO | WO 2007/089893 A1 | 8/2007 |

OTHER PUBLICATIONS

International Search Report—PCT/US2007/002743 (Jun. 14, 2007).
International Search Report—PCT/US2007/002741 (Jul. 9, 2007).
The Journal of Invasive Cardiology entitled "Use of a Second Buddy Wire During Percutaneous Coronary Interventions: A Simple Solution for Some Challenging Situations" dated Apr. 25, 2005, pp. 1-8.
Office Action dated Nov. 15, 2007 issued in related U.S. Appl. No. 11/652,430.
Office Action dated Mar. 17, 2008 U.S. Appl. No. 11/706,548 issued in related application.
Office Action dated Apr. 7, 2008 U.S. Appl. No. 11/699,174 issued in related application.
Office Action dated May 16, 2008 U.S. Appl. No. 11/763,355 issued in related application.
Office Action dated May 23, 2008 U.S. Appl. No. 11/652,430 issued in related application.
International Search Report—PCT/US2007/04827 & Opinion (Mar. 14, 2008).
Suppl) Notification of Transmittal of International Preliminary Report on Patentability—PCT/US2007/002743—(Jun. 3, 2008).
Office Action Restriction dated Jul. 2, 2008 U.S. Appl. No. 11/699,171 issued in related application.
International Search Report/Written Opinion—PCT/US2006/040843 (Feb. 7, 2007).
International Preliminary Report on Patentability—PCT/US2007/002741 (Jun. 25, 2008).
Office Action dated Oct. 20, 2008 U.S. Appl. No. 11/549,481 issued in related application.
Office Action dated Nov. 20, 2008 U.S. Appl. No. 11/763,355 issued in related application.
Office Action dated Nov. 21, 2008 U.S. Appl. No. 11/549,473 issued in related application.
Office Action dated Nov. 21, 2008 U.S. Appl. No. 11/699,171 issued in related application.
Office Action dated Dec. 11, 2008 U.S. Appl. No. 11/652,430 issued in related application.
International Preliminary Report on Patentability and Written Opinion (Jul. 24, 2008) PCT/US2007/001066.
Office Action dated Sep. 26, 2008 U.S. Appl. No. 11/706,548 issued in related application.

Office Action dated Oct. 7, 2008 U.S. Appl. No. 11/507,993 issued in related application.

Office Action dated Oct. 15, 2008 U.S. Appl. No. 11/699,174 issued in related application.

Advisory Action dated Mar. 6, 2009 U.S. Appl. No. 11/652,430 issued in co-pending application.

Office Action dated Mar. 30, 2009 U.S. Appl. No. 11/699,174 issued in co-pending application.

Office Action dated Apr. 7, 2009 U.S. Appl. No. 11/706,548 issued in co-pending application.

Office Action dated Apr. 14, 2009 U.S. Appl. No. 11/549,481 issued in co-pending application.

Office Action dated May 8, 2009 U.S. Appl. No. 11/699,171 issued in co-pending application.

Office Action dated May 14, 2009 U.S. Appl. No. 11/507,993 issued in coo-pending application.

International Search Report—PCT/US2006/042184 (Mar. 1, 2007.

International Search Report—PCT/US2007/001066 (Jun. 18, 2007).

International Search Report—PCT/US2007/004827 (Oct. 23, 2007).

* cited by examiner

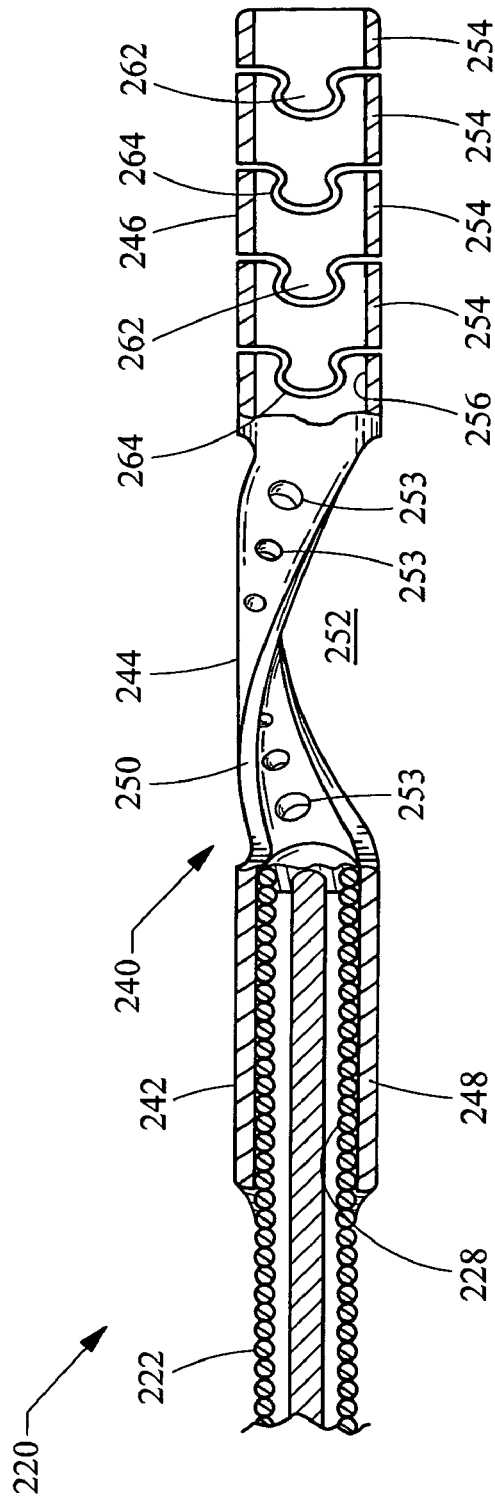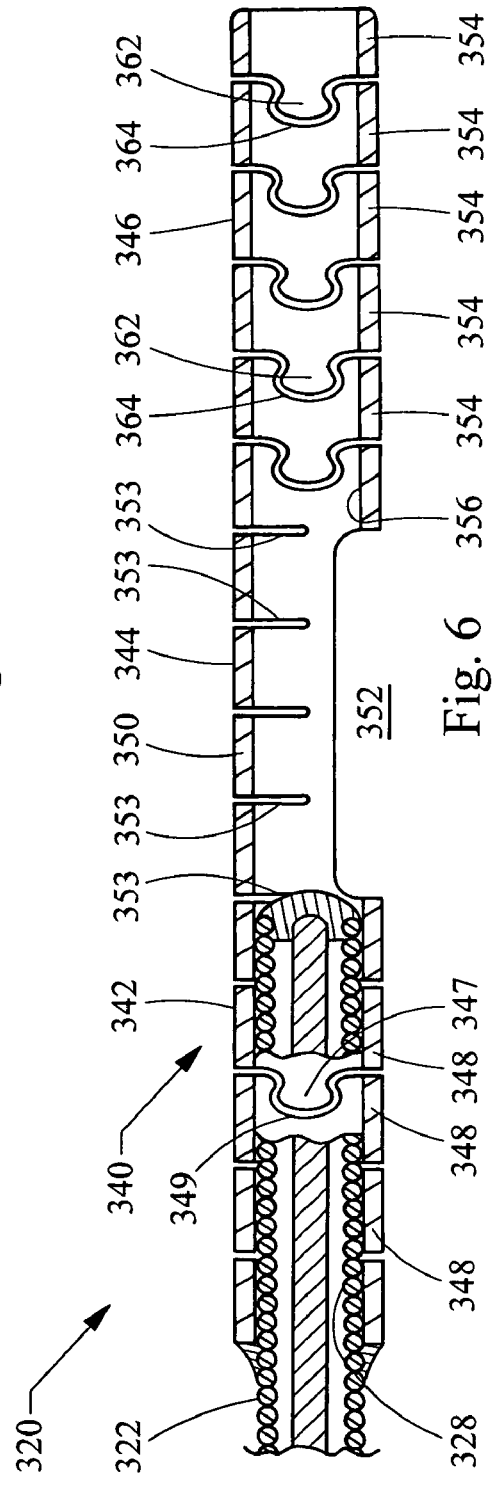

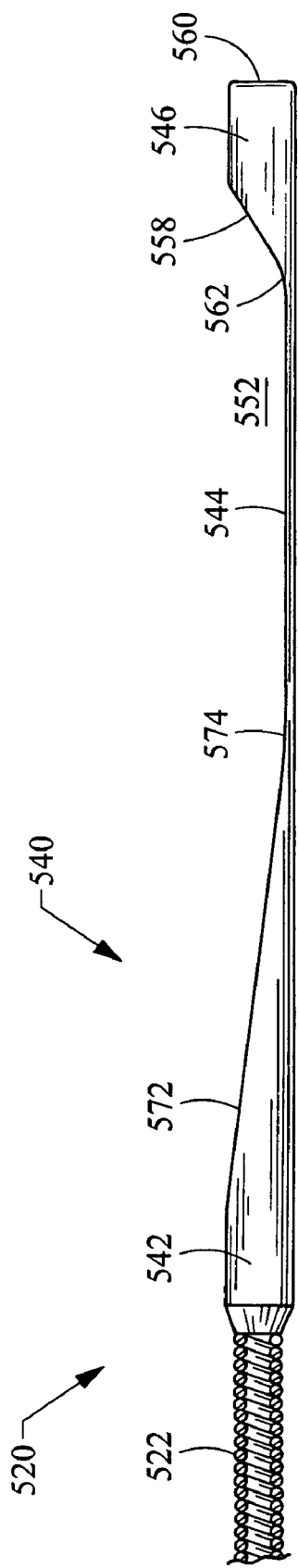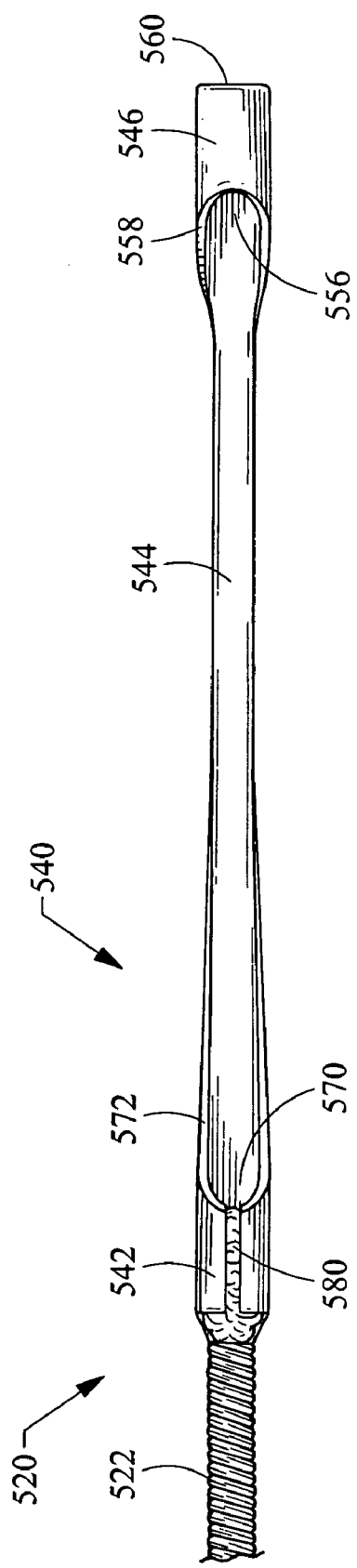
Fig. 9
Fig. 10

WIRE GUIDE HAVING DISTAL COUPLING TIP

CROSS-REFERENCE TO RELATED APPLICATIONS

This application claims the benefit of U.S. Provisional Applications Ser. No. 60/711,261, filed Jul. 25, 2006 and Ser. No. 60/711,261, filed on Aug. 25, 2005, entitled "WIRE GUIDE HAVING DISTAL COUPLING TIP," the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for percutaneous interventional procedures that may be easily and reliably traversed through the vasculature to a position proximate a previously introduced wire guide.

BRIEF SUMMARY OF THE INVENTION

The present invention provides a supporting wire guide for intracorporeal procedures that may be easily and reliably traversed through the vasculature to a position proximate a previously introduced wire guide. The supporting wire guide is a coupling wire guide that is structured to be slidably coupled to the previously introduced wire guide. In one embodiment constructed in accordance with the teachings of the present invention, the coupling wire guide generally includes a main body having a distal end, and a tip portion securely connected to the distal end of the main body. The tip portion includes first, second and third sections. The first section is connected to the main body, while the third section defines an axial passageway having a distal opening and a proximal opening. The axial passageway is sized to receive the previously introduced wire guide therein. The second section interconnects the first and third sections. and includes a strip extending axially and circumferentially to define a corresponding axially and circumferentially extending opening communication with the proximal opening.

The strip portion may include numerous features to provide increased flexibility to the tip portion, thereby facilitating translation of the coupling wire guide along the previously introduced wire guide. For example, the strip extends less than 360 degrees circumferentially to define the open area, and preferably has a width less 180 degrees (circumferentially). The strip may follow a curved path between the first and third sections, and preferably follows a helical path between the first and third sections, allowing the strip to both twist and bend a limited amount. The helical path preferably spans less than or equal to about 180 degrees circumferentially. The strip may also include a plurality of holes or slots therein to provide increased flexibility. The strip is also structured to guide the previously introduced wire guide relative to the proximal opening, and preferably guides the previously introduced wire guide away from the proximal opening and away from the strip. The distal end of the main body may also project into the open area and be curved to guide the previously introduced wire guide away from the main body.

Another embodiment of the coupling wire guide, constructed in accordance with the teachings of the present invention, also includes a main body having a distal end and a tip portion securely connected to the distal end. The tip portion includes first, second and third sections. The first section is connected to the main body and the second section interconnects the first and third sections. The second section includes a strip having a width less than 360 degrees circumferentially to leave an open area. The third section defines an axial passageway having a distal opening and a proximal opening in communication with the open area. The axial passageway is sized to receive the previously introduced wire guide therein. The third section comprises a plurality of interconnecting links providing flexibility to the third section.

According to more detailed aspects of this embodiment, the links each include at least one of a bulb or socket, the bulb and socket sized for interconnection. The strip may include one of a plurality of holes or a plurality of slots therein providing flexibility to the second section. The strip may follow a curved path between the first and third sections, or it may follow a straight path. The first section may also comprise a plurality of interconnecting links providing flexibility to the first section.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 5 is a cross-sectional view of another alternate embodiment of the coupling wire guide depicted in FIG. 1 constructed in accordance with the teachings of the present invention;

FIG. 6 is a cross-sectional view of yet another alternate embodiment of the coupling wire guide depicted in FIG. 1, constructed in accordance with the teachings of the present invention;

FIG. 9 is a side view of an alternate embodiment of the coupling wire guide depicted in FIG. 1 constructed in accordance with the teachings of the present invention; and FIG. 10 is a plan view of an the coupling wire guide depicted in FIG. 9.

DETAILED DESCRIPTION OF THE INVENTION

Figure 1:
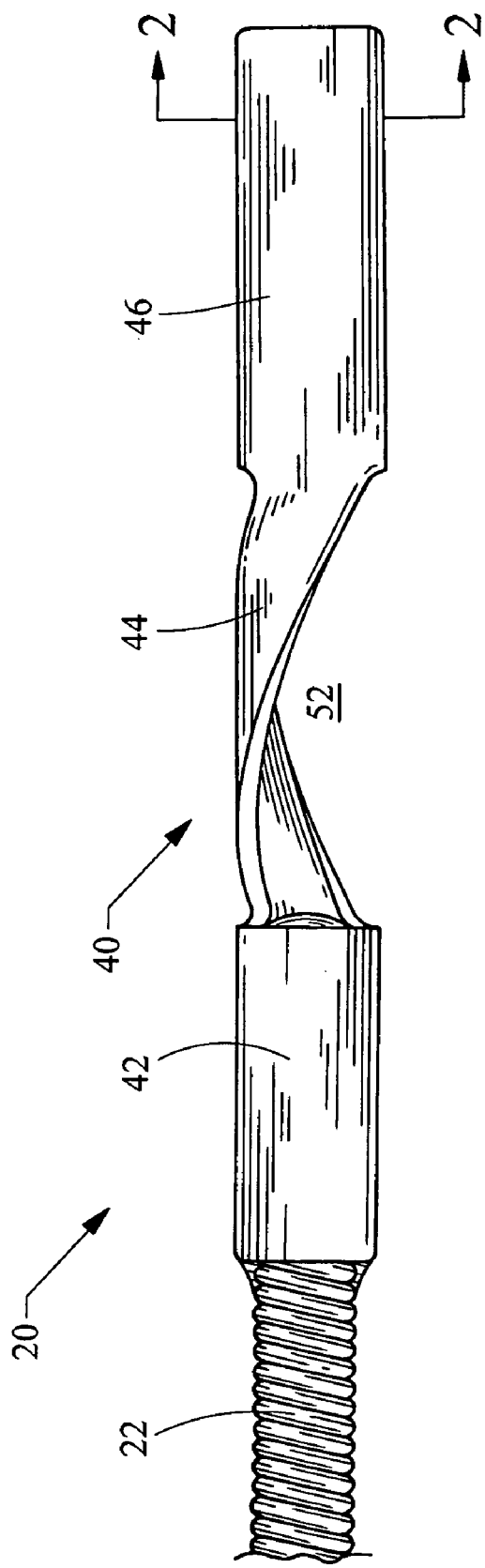
FIG. 1 is a side view of a coupling wire guide constructed in accordance with the teachings of the present invention.
Figure 2:
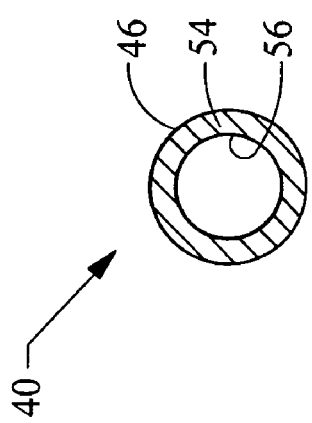
FIG. 2 is a cross-sectional view, taken about the line 2-2 in FIG. 1.
Figure 3:
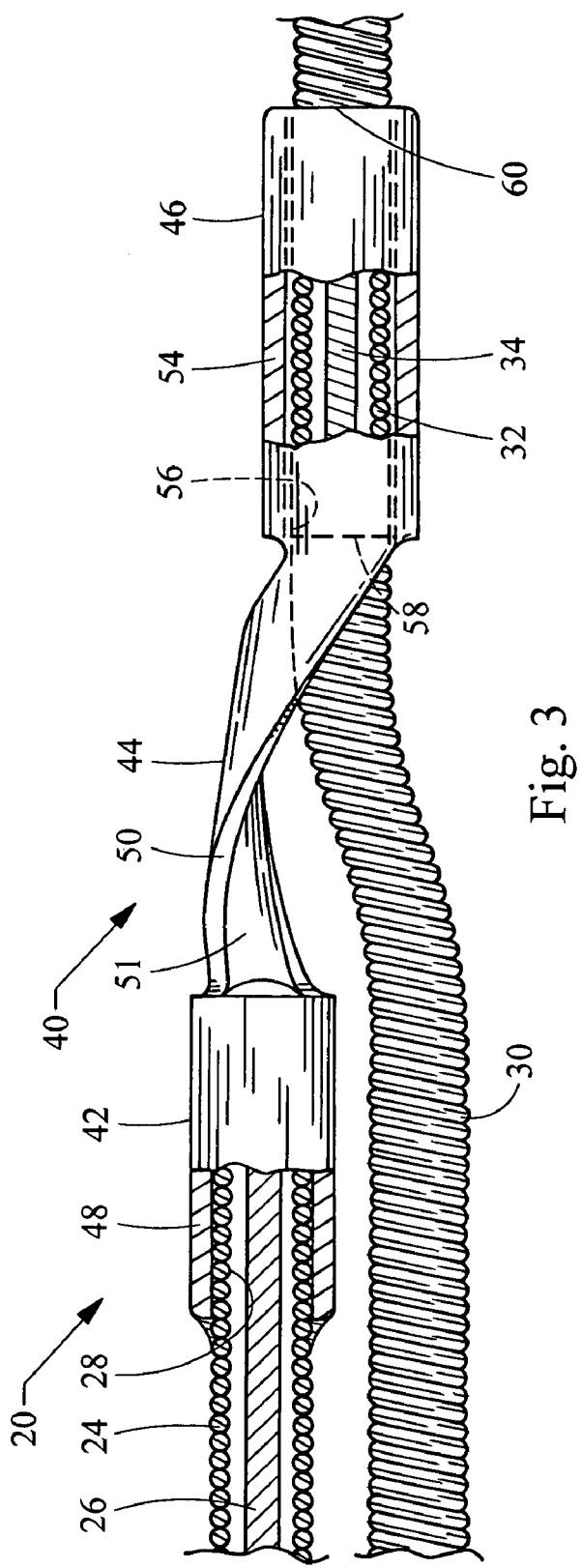
FIG. 3 is a side view, partially in cross-section and partially cut-away, showing the coupling wire guide of FIG. 1 coupled to a previously placed wire guide.

Turning now to the figures, FIGS. 1 to 3 depict a coupling wire guide 20 constructed in accordance with the teachings of the present invention. The coupling wire guide 20 includes a main body 22, which in FIG. 3 has been shown as a coil 24 disposed over a mandrel 26, a structure well known in the art. The main body 22 includes a distal end 28 which is connected to a tip portion 40 of the coupling wire guide 20. As will be described in detail below, the tip portion 40 is uniquely structured for slidably coupling the coupling wire guide 20 to a previously introduced wire guide 30, which has also been shown as comprising a coil 32 disposed over a mandrel 34 (FIG. 3). While wire guides are generally used in percutaneous interventional procedures, it will be recognized by those skilled in the art that the wire guide 20 of the present invention may also be employed in endoscopic or other intracorporeal procedures.

It will be recognized that the previously introduced wire guide 30, as well as the main body 22 of the coupling wire guide 20, may take numerous forms as many types of wire guides are known in the art, including a solid wire, tubular wires, coiled wires and combinations thereof. For example, the mandrel 26 of the main body 22 may be replaced with a safety wire, and likewise may not require a coil 24, but may simply comprise the mandrel itself or some variation thereof such as a solid wire mandrel having a coil tip section, such as is shown in U.S. Pat. No. 5,243,996.

As noted above, the tip portion 40 has been formed at the distal end 28 of the main body 22 to provide simple and reliable introduction of the coupling wire guide 20 over the previously introduced wire guide 30. The tip portion 40 is preferably constructed of a metal or alloy such as stainless steel or Nitinol, although other materials such as plastics may be used. A preferred method of manufacture includes laser cutting a cannula (or other tubular member), although other techniques such as molding, acid-etching or machining a solid rod may be employed. The tip portion 40 generally comprises a first section 42, a second section 44, and a third section 46. As best seen in FIG. 3, the first section 42 generally comprises a tubular member 48 that is sized to receive the distal end 28 of the main body 22. The tubular member 48 may be secured to the distal end 28 through welding or soldering, as well as through other secure bonding techniques such as adhesives, crimping or other deformation techniques, and the like. Preferably, the solder or other bonding material provides a smooth transition between the first section 42 of the tip portion 40 and the main body 22, as shown in the figures.

The second section 44 generally comprises a strip 50 which serves to provide flexibility to the tip portion 40 as well as guide the previously introduced wire guide 30 relative to the coupling wire guide 20. The strip 50 is sized to provide an opening or open area 52 (FIG. 1) for receiving the previously introduced wire guide 30 as shown in FIG. 3. To provide the open area 52, the strip extends less than 360 degrees circumferentially, and preferably has a width less than 180 degrees circumferentially. Specifically, the strip 44 follows a curved path between the first and third sections 42, 46, and as shown, preferably follows a helical path between the first and third sections 42, 46. In this manner, the strip 50 and second section 44 provide some degree of flexibility to the tip portion 40, while maintaining a suitable amount of rigidity and securely linking the first and third section 42, 46 and. For example, the strip 50 may both twist and bend, such that the third section 46 may rotate relative to the first section 42 (i.e. the coiling/uncoiling of the helical strip 50), and may also be tilted radially relative to the first section 42. Through use of the helical shape, the strip 50 is capable of bending in all directions, while at the same time maintaining suitable rigidity in all directions. Accordingly, the coupling wire guide 20 is increasingly adept at traversing the vasculature, and in particular tortuous pathways, while at the same time having sufficient rigidity for straightening out these passageways and passing through occlusions or other obstacles.

By way of the above-described structure, the helical strip 50 defines a guiding surface 51 which guides the previously introduced wire guide 30 relative to the third section 46. For example, when the strip 50 bends such that the third section 46 of the tip portion 40 moves downwardly, as shown in FIG. 3, the strip 50 is structured to guide the previously introduced wire guide 30 away from the third section 46 and away from the open area 52. In this manner, the strip 50 also assists in coupling the previously introduced wire guide 30 to the coupling wire guide 20.

The third section 46 of the tip portion 40 comprises a tubular member 54 defining an axial passageway 56 therein. As best seen in FIGS. 2 and 3, the axial passageway 56 is sized and structured to receive the previously introduced wire guide 30. The third section 46 and its axial passageway 56 also define a proximal opening 58 and a distal opening 60 through which the previously introduced wire guide 30 passes. The proximal opening 58 is thus in communication with the open area 52 defined by the second section 44 of the tip section.

Accordingly, it will be recognized by those skilled in the art that the tip portion 40 of the coupling wire guide 20 provides a simple and reliable slidable connection to a previously introduced wire guide 30. That is, the axial passageway 56 receiving the previously introduced wire guide 30 may be easily accessed by way of a large opening 52, which is defined by a strip 50 that assists in guiding the previously introduced wire guide 30 away from the passageway 56. Furthermore, the tip portion 40 is provided with sufficient flexibility that is helpful when traversing the coupling wire guide 20 through the vasculature, especially tortuous pathways, and along the previously introduced wire guide 30. At the same time, a secure connection is formed between the wire guides 20, 30, and the tip portion 40 of the coupling wire guide 20 has sufficient rigidity to translate the coupling wire guide 20 over the previously introduced wire guide 30 and pass through obstructed pathways, such as those having plaque or other lesions.

Figure 4:
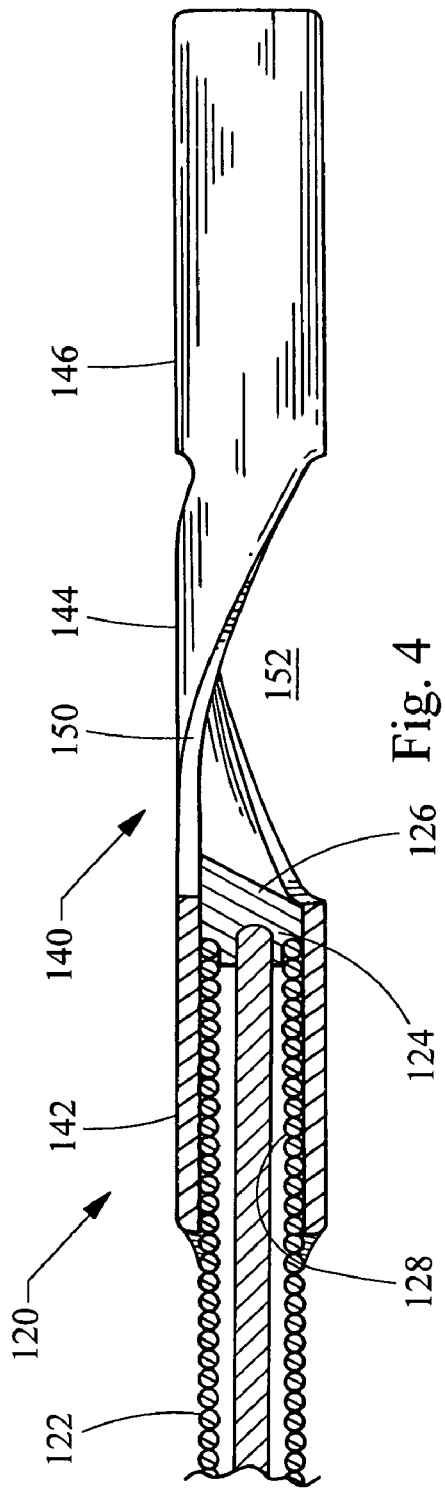
FIG. 4 is a side view, partially in cross-section and partially cut-away, of an alternate embodiment of the coupling wire guide depicted in FIG. 1 constructed in accordance with the teachings of the present invention.

An alternate embodiment of the coupling wire guide 120 has been shown in FIG. 4, constructed in accordance with the teachings of the present invention. In this embodiment, the tip portion 140 is of a substantially identical construction as described above with the embodiment depicted in FIGS. 1-3. As such, the tip portion 140 includes a first section 142, a second section 144, and a third section 146. The first section 142 is coupled to a main body 122, and particularly a distal end 128 of the main body. The second section 144 includes a strip 150 defining an open area, while the third section 146 receives the previously introduced wire guide (not shown).

In this embodiment, the distal end 128 of the main body 122 is constructed to include an end cap 124 which projects into the open area 152 defined by the second section 144. Notably, this end cap 124 includes an angled surface 126, designed to facilitate translation of the previously introduced wire guide away from the open area 152. It will be recognized that numerous other structures and shapes may be given to the end cap 124 to facilitate translation of the coupling wire guide 120 relative to the previously introduced wire guide, such as beveled or curved in one or multiple dimensions.

Another alternate embodiment of the coupling wire guide 220 has been depicted in FIG. 5 constructed in accordance with the teachings of the present invention. As in the prior embodiments, the coupling wire guide 220 generally includes a main body 222 having a tip portion 240 constructed at a distal end 228 thereof. The tip portion 240 generally includes a first section 242 defined by a tubular member 248 securely connected to the distal end 228.

In this embodiment, the second section 244 includes a strip 250 which interconnects the first and third sections 242, 246 of the tip portion 240 and defines an open area 252. The strip 250 is structured similarly to the prior embodiments, and has a similar width and follows a similar curved helical path. However, in this embodiment the strip 250 has been formed with a plurality of holes 253 along its length. In this manner, the second section 244 and strip 250 are provided with increased flexibility, thereby providing increased mobility of the third section 246 relative to the first section 242 and main body 222. It will be recognized that the holes 253 may take many sizes and shapes, and may include varying sizes such as is shown in FIG. 5.

Similarly, the third section 246 has been structured to improve the flexibility thereof. In particular, the third section 246 is constructed of a plurality of links 254 which are interconnected to form an axial passageway 256 sized to receive the previously introduced wire guide. Each link 254 includes at least one of a bulb 262 or socket 264 which are sized and structured for secure interconnection. In this manner, the third section 246 of the tip itself may bend in all directions to further improve the translation of the coupling wire guide 220 through the vasculature, while also providing sufficient rigidity for such movement.

Yet another alternate embodiment of the coupling wire guide 320 has been depicted in FIG. 6, constructed in accordance with the teachings of the present invention. As in the prior embodiments, the coupling wire guide 320 includes a main body 322 that includes a tip portion 340 connected to a distal end 328 thereof. The tip portion 340 includes a first section 342, a second section 344 and a third section 346. The first section 342 is coupled to the distal end 328 of the main body 322 as previously discussed in prior embodiments. However, in this embodiment the first section 342 is also constructed of a plurality of individual links 348. The links 348 each include at least one of a bulb 347 or socket 349 which are sized and structured for interconnection. In this manner, the first section 342 of the tip portion 340 is also provided with increased flexibility to improve placement of the coupling wire guide 320.

The second section 344 of the tip portion 340 includes a strip 350 which follows a straight path and preferably spans about 270 degrees circumferentially to define an open area 352. Here, the strip 350 has been provided with a plurality of slots 353 which span a substantial portion of the width of the strip 350. It can therefore be seen that the second section 344 of the tip portion 340 is also provided with increased flexibility to improve placement of the coupling wire guide 320.

Finally, and similar to the prior embodiment discussed and shown in FIG. 5, the third section 346 includes a plurality of individual links 354 having at least one of a bulb 326 or socket 364 which are sized and structured for secure interconnection. The plurality of links 354 combine to define an axial passageway 356 which is in communication with the open area 352, thereby providing a pathway through which the coupling wire guide 320 may be coupled to the previously introduced wire guide (not shown).

Figure 7:
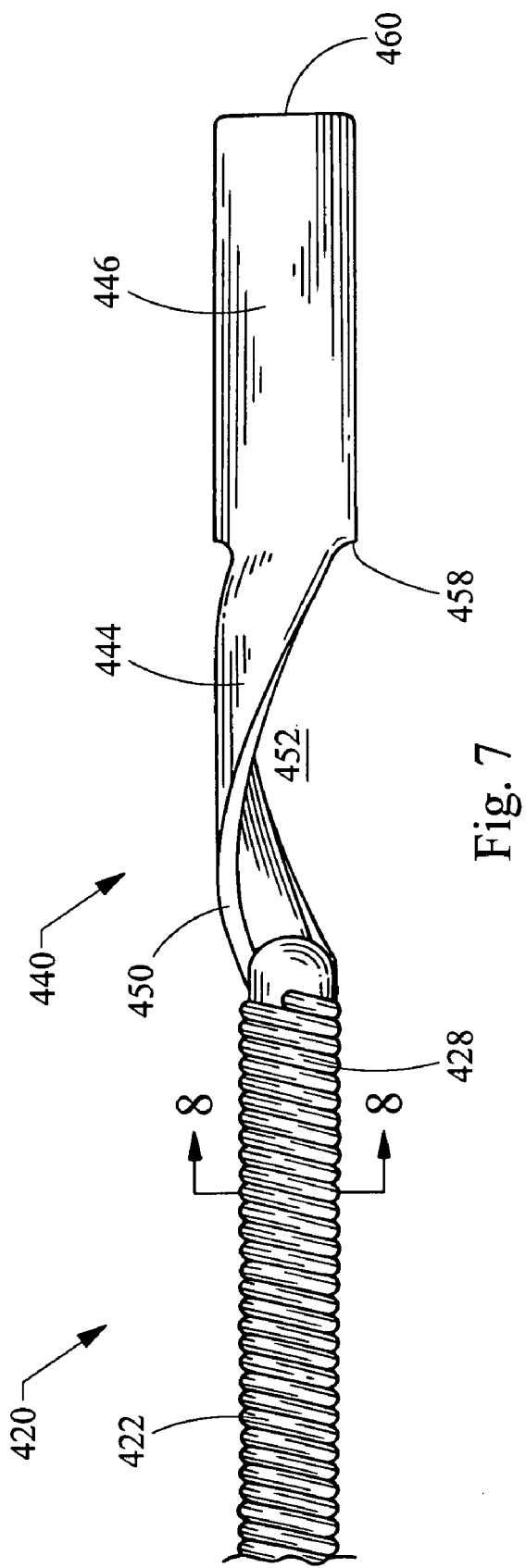
FIG. 7 is a side view of still yet another alternate embodiment of the coupling wire guide depicted in FIG. 1 constructed in accordance with the teachings of the present invention.
Figure 8:
FIG. 8 is a cross-sectional view taken about the line 8-8 in FIG. 7.

Turning to FIGS. 7 and 8, still yet another alternate embodiment of the coupling wire guide 420 has been depicted. As in the prior embodiments, the coupling wire guide 420 includes a main body 422 that includes a tip portion 440 connected to a distal end 428 thereof. The tip portion 440 includes a first section 442 (FIG. 8), a second section 444 and a third section 446. The second and third sections 444, 446 are constructed similar to the prior embodiments, and define a large opening 452 leading to proximal and distal openings 458, 460 respectively.

The first section 442 is coupled to the distal end 428 of the main body 422 as previously discussed in prior embodiments. However, in this embodiment the first section 442 is formed as a strip 443, rather than a tubular member. The strip 443 has a curved, and preferably semi-circular, cross-sectional shape as best seen in FIG. 8, and is straight in the axial direction, although it could follow a curved path similar to the curvature of the strip 450 of the second section 444. The strip 443 has been shown spanning about 90 degrees circumferentially, although it may take any size. By utilizing a strip 443 as the first section 442, it is easier to bond, weld or solder the first section 442 to the distal end 428. Additionally, the strip 443 provides a smaller profile to the tip portion 440, thereby improving its ability to traverse the vasculature.

Another alternate embodiment of a coupling wire guide 520 is depicted in FIGS. 9 and 10. As in the prior embodiments, the coupling wire guide 520 includes a main body 522 and a tip portion 540 connected to a distal end thereof. The tip portion 540 includes a first section 542, a second section 544 and a third section 546. The second section 546 is formed as a linear strip defining a large opening 552, and also serves to interconnect the first and second sections 542, 546. The third section 546 defines an axial passageway 556 having a proximal opening 558 and a distal opening 560.

In this embodiment, the proximal end of the third section 546 (i.e. where the second section 544 transitions into the third section 546) is beveled, and likewise the distal portion of the first section 542 (i.e. where the first section 542 transitions into the second section 544) is beveled. Stated another way, the proximal opening 558 in the third section 546 is oriented on an angle (less than 90 degrees) relative to the central axis of the coupling tip 540, and likewise the distal opening 572 of the first section 542 is oriented on an angle relative to the central axis. In this manner, when the coupling wire guide 520 has been disconnected from the previously introduced wire guide within the body (or whenever the coupling wire 520 is used alone), the smooth beveled transition between the sections 542, 544, 546 of the coupling tip 540 serves to make the coupling tip 540 more atraumatic and minimize the potential for disturbing the vasculature, lesions, protuberances or other structures such as deployed stents, etc. Preferably, the bevel angle is in the range of about 5 to 45 degrees (relative to the central axis of the coupling tip 540). In the embodiment depicted, the angle of proximal opening 558 is about 30 degrees, and the angle of distal opening 572 is about 7 degrees. It will also be seen that the beveled openings 558, 572 include a radiused fillet 562, 574 where they meet the second section 544.

The first section 542 is coupled to the distal end of the main body 522, preferably by welding as discussed in the prior embodiments. Most preferably, the first section 542 is formed as a tubular structure having a slot where a weld 580 is formed between the first section 542 and the main body 522. The areas at the ends of the tubular first section 542 may also be welded. In a preferred construction, all components of the main body 522 and coupling tip 540 are formed of a stainless steel to facility welding and uniformity of the coupling wire guide 520.

Accordingly, it will be recognized by those skilled in the art that the coupling wire guide provides simple and reliable coupling to a previously introduced wire guide through the provision of a large open area leading to an axial passageway structured to receive the previously introduced wire guide. At the same time, structures are provided to direct the previously introduced wire guide out of the open area and axial passageway. Furthermore, the tip portion is provided with a number of different features which provide increased flexibility to the tip portion of the coupling wire guide, while maintaining sufficient rigidity and strength. In this manner, the coupling wire guide is increasingly adept at traversing the vasculature, and in particular tortuous pathways, while at the same time having sufficient rigidity for straightening out these passageways and passing through occlusions or other obstacles.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for coupling to a previously introduced wire guide in intracorporeal procedures, the coupling wire guide comprising:
    a main body having a distal end;
    a tip portion securely connected to the distal end of the main body, the tip portion including first, second and third sections oriented along a longitudinal axis, the first section connected to the main body, the second section interconnecting the first and third sections, the third section defining an axial passageway having a distal opening and a proximal opening, the axial passageway sized to receive the previously introduced wire guide therein; and
    the second section including a strip extending axially and circumferentially that defines a complementary axially and circumferentially extending opening in communication with the proximal opening, the strip following a curved path between the first and third sections, the strip extending circumferentially around the longitudinal axis less than 360 degrees and having a circumferential width less than 180 degrees, the natural unbiased configuration of the tip portion defining the axially and circumferentially extending opening.

2. The coupling wire guide of claim 1, wherein the strip extends circumferentially around the longitudinal axis less than or equal to 180 degrees.

3. The coupling wire guide of claim 1, wherein the strip follows a helical path between the first and third sections.

4. The coupling wire guide of claim 3, wherein the helical path extends less than or equal to about 180 degrees circumferentially.

5. The coupling wire guide of claim 1, wherein the strip is structured to guide the previously introduced wire guide relative to the proximal opening.

6. The coupling wire guide of claim 5, wherein a distal end of the strip is structured to guide the previously introduced wire guide away from the proximal opening.

7. The coupling wire guide of claim 5, wherein a proximal end of the strip is structured to guide the previously introduced wire guide away from the strip.

8. The coupling wire guide of claim 1, wherein the strip includes a plurality of holes or slots therein providing flexibility to the strip.

9. The coupling wire guide of claim 1, wherein the first section of the tip portion is tubular, and wherein the main body extends through the tubular first section and defines a closed distal end surface located proximate the axially and circumferentially spaced opening.

10. The coupling wire guide of claim 9, wherein the tip portion is welded, bonded, or soldered to the main body.

11. The coupling wire guide of claim 9, wherein the distal end of the main body projects into the axially and circumferentially_extending opening.

12. The coupling wire guide of claim 11, wherein the distal end surface of the main body defines a guide surface exposed to the axially and circumferentially extending opening to guide the previously introduced wire guide away from the distal end of the main body.

13. The coupling wire guide of claim 11, wherein the distal end of the main body is angled less than 90° relative to a longitudinal axis of the tip portion and defines a guide surface exposed to the opening to guide the previously introduced wire guide away from the distal end of the main body.

14. The coupling wire guide of claim 1, wherein the proximal opening faces axially.

15. The coupling wire guide of claim 1, wherein the proximal end of the third section is beveled.

16. The coupling wire guide of claim 15, wherein the distal end of the first section is beveled.

17. The coupling wire guide of claim 15, wherein the proximal opening in the third section is angled between 5 and 45 degrees relative to the central axis of the coupling tip.

18. The coupling wire guide of claim 16, wherein the distal opening in the first section is angled between 5 and 45 degrees relative to the central axis of the coupling tip.

19. The coupling wire guide of claim 16, wherein the proximal opening in the third section is angled about 30 degrees, and the distal opening in the first section is angled about 7 degrees.

20. The coupling wire guide of claim 1, wherein the first and third sections of the tip portion are coaxial in the natural unbiased configuration of the tip portion.

21. A coupling wire guide for coupling to a previously introduced wire guide in intracorporeal procedures, the coupling wire guide comprising:
a main body having a distal end;
a tip portion securely connected to the distal end of the main body, the tip portion including first, second and third sections oriented along a longitudinal axis, the first section connected to the main body, the second section interconnecting the first and third sections, the third section having a solid tubular wall defining an axial passageway having a distal opening and a proximal opening, the axial passageway sized to receive the previously introduced wire guide therein; and
the second section including a strip extending axially and circumferentially that defines a complementary axially and circumferentially extending opening in communication with the proximal opening, the strip following a helical path between the first and third sections, the helical path making less than one turn around the longitudinal axis.

22. The coupling wire guide of claim 21, wherein the helical path makes less than or equal to one-half turn around the longitudinal axis.

23. The coupling wire guide of claim 21, wherein the distal end of the main body projects into the opening, and the distal end of the main body is angled less than 90° relative to a longitudinal axis of the tip portion and defines a guide surface exposed to the opening to guide the previously introduced wire guide away from the distal end of the main body.

24. The coupling wire guide of claim 21, wherein the distal end of the main body projects into the axially and circumferentially extending opening, and the distal end of the main body has a closed distal end surface that defines a guide surface exposed to the axially and circumferentially extending opening to guide the previously introduced wire guide away from the distal end of the main body.

25. A coupling wire guide for coupling to a previously introduced wire guide in intracorporeal procedures, the coupling wire guide comprising:
a main body having a distal end;
a tip portion securely connected to the distal end of the main body, the tip portion including first, second and third sections oriented along a longitudinal axis, the first section connected to the main body the second section interconnecting the first and third sections, the third section defining an axial passageway having a distal opening and a proximal opening, the axial passageway sized to receive the previously introduced wire guide therein, the second section including a strip extending axially and circumferentially that defines a complementary axially and circumferentially extending opening in communication with the proximal opening, the strip following a curved path around the longitudinal axis having less than one turn; and
the tip portion including a cannula having a material void between the ends of the cannula to define the first, second and third sections of the tip portion and the strip of the second section.

26. The coupling wire guide of claim 25, wherein the tip portion is constructed of Nitinol or stainless steel.

27. The coupling wire guide of claim 25, wherein the tip portion is welded or soldered to the main body.

28. The coupling wire guide of claim 25, wherein the material void has opposing ends that are spaced from the ends of the cannula.

29. The coupling wire guide of claim 25, wherein the strip has a semi-annular cross section.

30. The coupling wire guide of claim 25, wherein the curved path of the strip make less than or equal to one-half turn.

* * * * *